United States Patent [19]
Wiggins et al.

[11] Patent Number: 5,865,272
[45] Date of Patent: Feb. 2, 1999

[54] DIFFERENTIAL DRIVE LINEAR ACTUATOR

[75] Inventors: Christopher R. Wiggins, Trowbridge; Peter G. Sanders, Frome, both of Great Britain

[73] Assignee: Rotork Controls Limited, Bath, United Kingdom

[21] Appl. No.: 750,226
[22] PCT Filed: Jul. 14, 1995
[86] PCT No.: PCT/GB95/01666
 § 371 Date: Nov. 22, 1996
 § 102(e) Date: Nov. 22, 1996
[87] PCT Pub. No.: WO96/04494
 PCT Pub. Date: Feb. 15, 1996

[30] Foreign Application Priority Data

Aug. 3, 1994 [GB] United Kingdom ............ 9415648

[51] Int. Cl.⁶ .................................................. F16H 25/20
[52] U.S. Cl. ............................... 185/40 R; 74/424.8 VA
[58] Field of Search .................... 74/424.8 VA, 89.15;
            185/40 R; 251/69, 71, 129.11, 129.12

[56] References Cited

U.S. PATENT DOCUMENTS

| | | | |
|---|---|---|---|
| 3,505,888 | 4/1970 | Denkowski | 74/89.15 |
| 3,640,140 | 2/1972 | Gulick et al. | 74/89.15 |
| 4,090,589 | 5/1978 | Fitzwater | 185/40 R |
| 4,256,065 | 3/1981 | Hirt | 74/424.8 VA X |
| 5,129,273 | 7/1992 | Fukui et al. | 74/89.15 |
| 5,195,721 | 3/1993 | Akkerman | 74/424.8 VA X |
| 5,472,065 | 12/1995 | Vergin | 185/40 R |

FOREIGN PATENT DOCUMENTS 838009  9/1949  Germany.

*Primary Examiner*—Charles A. Marmor
*Assistant Examiner*—Troy Grabow
*Attorney, Agent, or Firm*—Stetina Brunda Garred & Brucker

[57] ABSTRACT

A linear actuator having an output shaft having a pair of driven wheels mounted thereon. One of the driven wheels is rotatably mounted in a fixed plane and has a drive nut for an associated thread on the output shaft. The other drive wheel is rotatably fixed to the output shaft. An input shaft is in side-by-side relationship with the output shaft and adapted to be rotated by a suitable power source. The input shaft provides a drive wheel for each of the driven wheels, with the ratio between each drive and driven wheel set being chosen to rotate the driven wheels at different speeds in the same rotational direction and thereby produce a controlled axial movement of the output shaft in a direction depending upon the relative rotation of the driven wheels. The other driven wheel and the drive wheel of its set are in the form of meshing helical gear wheels. A fail-safe arrangement is provided and has a clutch between the drive wheels of the input shaft, a back-drive for the output shaft, and biasing means for effecting a back-drive. The arrangement is such that the meshing helical gears impart an axial force to engage the clutch only while power is supplied, and the biasing means are operative to back-drive the output shaft to a fail-safe position when the power is terminated.

10 Claims, 4 Drawing Sheets

DIFFERENTIAL DRIVE LINEAR ACTUATOR

BACKGROUND OF THE INVENTION

This invention relates to actuators of the type comprising an output shaft which, in use, effects an axial movement, and drive means therefor. In particular the output shaft is intended to effect a controlled, slow moving, extending or retracting axial movement for operating an associated mechanism. A particular application for such actuators is for driving the valve spindle of a valve, where the spindle is extended or retracted in order to force a valve sealing element against the valve seat.

In most existing designs of actuators of the type referred to above, the axial movement of the output shaft is obtained by arranging for a power source to drive the worm of a worm and worm wheel set to effect a single stage reduction in speed, varying typically between 15 to 1 to 80 to 1. The worm wheel rotates a drive nut which is threaded on to the valve spindle so that rotation of the drive nut extends or retracts the output shaft.

There are two applications where this type of actuator introduces installation and operating problems. Firstly, there are applications where the plan area for the equipment is restricted to a relatively small diameter. This occurs in under-sea equipment where the gear box and motor has to be encased in chambers subjected to high external pressures. Also in nuclear reactor engineering and similar sites producing ionising radiation the equipment has to pass through the biological shielding and hence apertures in the shield must be of the smallest possible diameter.

Secondly, there are applications where the equipment must be of the fail-safe type—in the case of a valve, the spindle must move under spring force to one or other terminal position upon failure of the power supply. The conventional actuator is not, normally, suitable for this duty as the drive nut will not normally "back drive" when a force is applied to the spindle.

SUMMARY OF THE INVENTION

According to the present invention there is provided an actuator of the type discussed above, and comprising an output shaft having a pair of driven wheels mounted thereon, one being rotatably mounted in a fixed plane and having a drive nut for a thread on said output shaft, the other being rotatably fixed to said output shaft, and an input shaft in side-by-side relationship with said output shaft adapted to be rotated by a suitable power source, said input shaft providing a drive wheel for each of the driven wheels, the ratio between each drive and driven wheel set being chosen to rotate the driven wheels at different speeds in the same rotational direction to produce a controlled axial movement of the output shaft in a direction depending upon the relative rotation of said driven wheels, wherein said other driven wheel and the drive wheel of its set are in the form of meshing helical gear wheels, and wherein a fail-safe arrangement is provided comprising a clutch between the drive wheels of the input shaft, a back-drive for said output shaft, and biasing means for effecting a back-drive, the arrangement being such that the meshing helical gears impart an axial force to engage the clutch only while power is supplied and the biasing means are operative to back-drive the output shaft to a fail-safe position when the power is terminated.

Preferably, an electromagnet or other suitable force applying means is provided and adapted to maintain the clutch in engagement when power is terminated.

In one arrangement, said other driven wheel may be axially fixed on said output shaft, whereby the speed difference between the driven wheels will cause this wheel and hence the output shaft to move axially towards or away from said one driven wheel depending upon the relative rotation of said driven wheels.

In another arrangement, said other driven wheel may also be in a fixed plane and said output shaft may be axially movable relative to said other driven wheel via an axially extending key/keyway arrangement, whereby the speed difference between the driven wheels will cause movement of the output shaft in an axial direction depending upon the relative rotation of said driven wheels.

An actuator in accordance with the invention can achieve high effective gear ratios (in excess of 100 to 1) using only two gear connections which, in turn enables a relatively coarse thread to be used on the output shaft; in particular, the pitch helix angle can be sufficiently large to facilitate back-driving of the output shaft, since in the event of a power failure, the force applied by the biasing means will provide a significant axial movement of the output shaft to its "fail-safe" position, the drive nut being free to rotate because the clutch is dis-engaged.

BRIEF DESCRIPTION OF THE DRAWINGS

In order that the invention may be readily understood and further features made apparent, two embodiments and modifications of the invention will now be described, by way of example, with reference to the accompanying drawings in which.

DETAILED DESCRIPTION OF THE PREFERRED EMBODIMENTS

Figure 1:
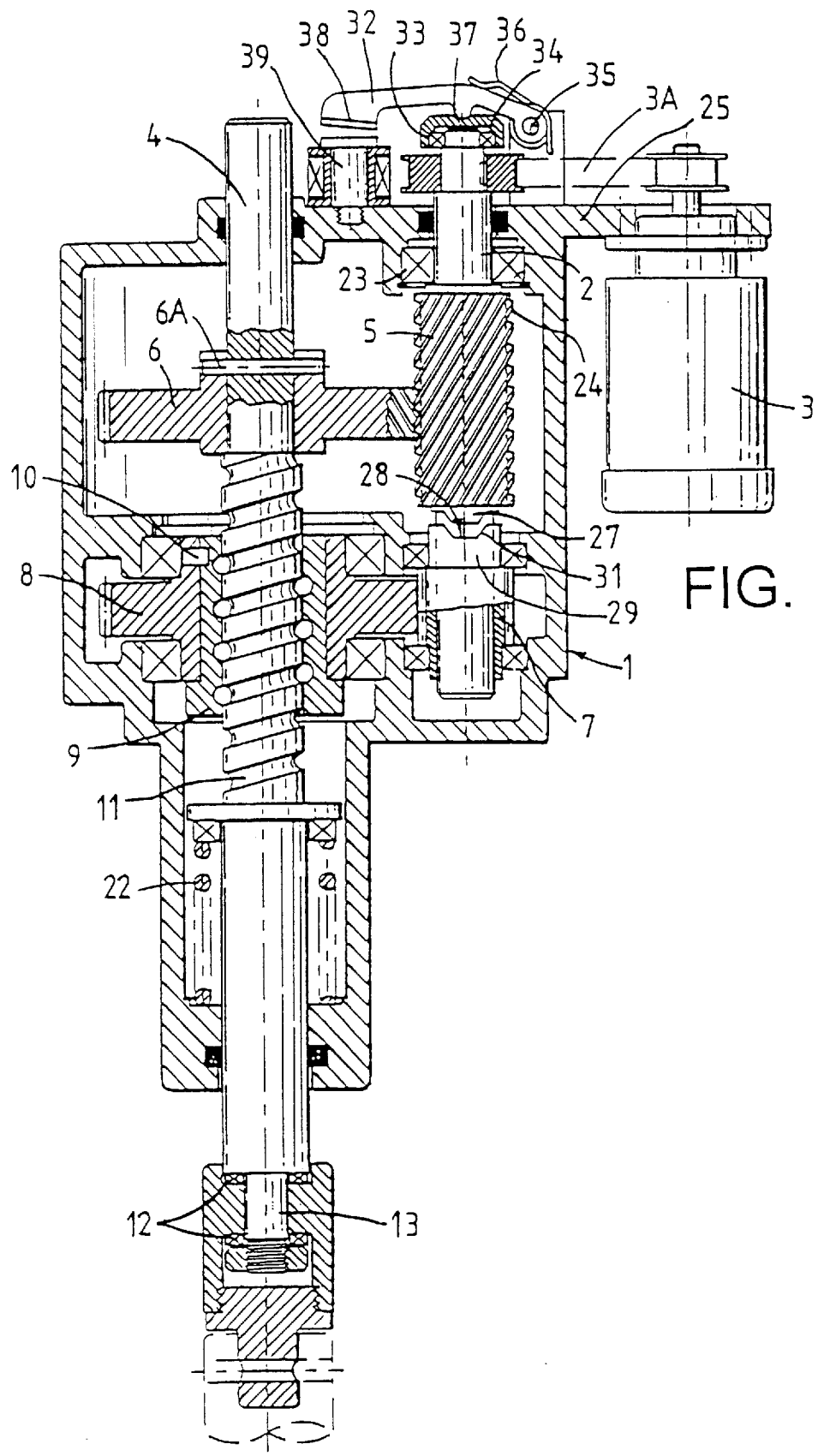
FIG. 1 is a section through a simplified mechanical layout of the first embodiment of actuator.

Referring to FIG. 1 the actuator comprises a gear box 1 having an input drive shaft 2, to which a drive motor 3 can be connected via driving gear or, as shown, a belt pulley 3A, and an output shaft in the form of a spindle 4 which is positioned adjacent and parallel to the input shaft and is capable of movement in either axial direction. A pinion 5 is fixed to, or made integral with the input shaft 2; this pinion is elongated to a length at least equal to the sum of the full axial travel of the spindle 4 and the effective tooth face width of an associated gear wheel 6 on the spindle. This is to ensure that the gear wheel 6, which is made fast to the spindle 4 by means of a pin 6A, stays in mesh with the elongated pinion 5 over the full axial travel of the spindle 4. A second pinion 7 is free to rotate relative to the input shaft 2 but can be clutched to the input shaft by the action of a clutch mechanism shown dis-engaged in FIG. 1. The two halves of the clutch are formed by dogs 27 located on the lower end of the elongated pinion 5 and cooperating recesses 28 formed in a clutch ring 29 which is integral with the second pinion 7. The second pinion 7 is arranged to have a small increase in its tooth pitch circle diameter (p.c.d.) compared to the said pinion 5 and to mesh with an associated gear wheel 8, on the spindle 4, having a corresponding decrease in its tooth p.c.d. in order to maintain the correct centre distance between the input shaft 2 and the said spindle. The second pinion 7 and meshing gear 8 may be straight spur gears or helical gears.

The gear wheel 8 is mounted on the spindle 4 via a recirculating ball nut 9 which meshes with a mating half-round thread 11 on the spindle 4. The ball nut 9 is constrained to rotate with the gear wheel 8 by means of a pin 10.

Rotation of the input shaft 2 will thus rotate and thereby move the spindle 4 axially as the following example, giving specific gear teeth data will demonstrate:
Pinion 5 has 16 helical teeth—Metric Module 3
Gear Wheel 6 has 51 helical teeth—Metric Module 3
At 1000 r.p.m. clockwise rotation, viewed from above (for subsequent description—all rotations are viewed from above) on input shaft 2, the spindle 4 will be rotated anti-clockwise at a speed of $$1000 \times 16/51 = 313.73 \ r.p.m.$$

Second pinion 7 has 17 helical teeth—Metric Module 3
Gear Wheel 8 has 50 helical teeth—Metric Module 3
At 1000 r.p.m. clockwise rotation on input shaft 2 (clutch engaged) the gear wheel 8 with ball nut 9 will rotate anti-clockwise at a speed of $$1000 \times 17/50 = 340.00 \ r.p.m.$$

The effective axial movement of the ball nut 9 on the spindle 4 depends on the relative rotational speed of the spindle 4 and the gear wheel 8—i.e.

$$313.73 - 340.00 = -26.27 \ r.p.m.$$

If the spindle thread is given a 5 mm lead and is right handed, the spindle will extend from the gear box at a speed of $$26.27 \times 5 = 131.37 \ mm \ per \ minute \ per \ 1000 \ r.p.m. \ of \ input \ shaft \ 2$$

The end of the spindle 4 is rotating as the spindle advances or retracts—in the example given, the rotation is equal to 313.73 r.p.m. per 1000 r.p.m. of the input shaft 2. For applications where the spindle terminates in an "eye" or "clevis" for the attachment of a lever, or for the attachment of a non-rotating valve spindle, it is necessary to provide thrust bearings 12 and a journal bearing 13 to eliminate the rotation from the equipment being operated by the actuator.

It will be appreciated that such a drive arrangement produces a relatively small difference in ratios between the two gear meshes 5, 6 and 7, 8. In the foregoing example, this is achieved with a common shaft centre distance by using a common tooth module size and helix angle and keeping the sum of the teeth for each mesh equal. It will also be appreciated that other arrangements can be used to maintain the common shaft centre distance, for example, using different gear module sizes and changing the helix angle for each mesh without departing from the scope of the invention.

In applications where the overall length and cross-sectional plane of the actuator need to be kept as small and compact as possible, advantageously the drive motor 3 would be mounted on the same axis as the actuator spindle. Thus, referring to FIG. 2, the drive motor is shown mounted directly over the axis of the spindle 4 and is provided with a hollow drive shaft 15 with the end 16 of the spindle 4 accomodated within the bore of the shaft 15. Gear teeth 17 machined on the end of the motor shaft 15 mesh with a gear wheel 18 mounted and keyed to the input shaft 2. A bearing 19 is provided in the end of the drive shaft 15, the bearing being of a type which permits axial as well as rotational movement of the plain end 16 of the spindle 4.

In accordance with the present invention, the actuator is provided with a fail-safe function. For this duty it is required that the spindle shall move to the "safe" end of travel position under the action of a spring force or other applied force if the energy supply to the motor fails or if the motor and its associated input drive mechanism seizes. A related requirement to this last situation is that the motor and input drive mechanism, which is normally only designed to move the output spindle relatively slowly, can be isolated from the spindle drive by remote means so that the spring force can be used to give a rapid return of the spindle to the "safe" end of travel position. Thus, the assembly consisting of the half-round thread 11 and the meshing recirculating ball nut 9 is designed to be "back-driven". To achieve this, the spindle 4 is provided with a spring 22 and the axial force of the spring is sufficient to rotate the gear wheel 8 and pinion 7 by acting on the ballscrew assembly, provided that the pinion 7 is uncoupled from the input drive. To achieve uncoupling of the pinion, the input drive shaft 2 is capable of a limited amount of axial movement within an upper bearing 23 securely retained within a counterbore 24, in the top wall 25 of the gear box 1. As mentioned hereinbefore a clutch mechanism is provided between the lower end of the elongated pinion 5 and the clutch ring 29, which enables the pinion 7 to be locked to the elongated pinion 5 when the shaft 2 is moved axially downwards through said upper bearing 23; the clutch halves comprising the dogs 27 and co-operating recesses 28 are provided with angled contact surfaces 31.

The upper end of the input shaft 2 projects, via the counterbore 24, through the top wall 25, where a lever 32 is arranged to bear on the shaft end via a cap 33 and bearing 34. The lever pivot 35 is provided with a light clock spring 36 to ensure that the lever re-acting surface 37 stays in contact with the shaft cap 33 and exerts a light pressure thereon. At the free end of the lever 32 is mounted the pole piece 38 of a holding electro-magnet 39.

The clutch (27 and 29) is shown in the dis-engaged state with the spindle 4 travelling towards, or at, its fail-safe position under the action of the spring 22. In this state power is not being supplied to the motor 3, or to the holding magnet 39. With the ball screw lead angle illustrated in FIG. 1, the effect of the spring force on the spindle 4 is to try to rotate the gear wheel 8 clockwise by back-driving the ball screw nut 9 and, simultaneously, to rotate the gear wheel 6 anti-clockwise. The corresponding relative rotations on the pinion 7 and the elongated pinion 5, tends to cause the disengagement of the clutch members 27 and 29 on the input shaft 2 and cause this shaft to move upwards to the position shown in FIG. 1.

If the input drive shaft 2, with the elongated pinion 5 is now rotated clockwise, by supplying power to the motor 3, the helix angle on the helical pinion 5 will cause the shaft 2 to move axially in a downward direction, as illustrated, bringing the clutch members 27 and 29 into engagement. If power is simultaneously applied to the holding magnet 39, then, once the engaged position is reached, the magnet pole piece 38 will exert sufficient downward force on the shaft 2, via the reacting surface 37 and cap 33, to maintain the clutch in engagement against the parting action of the spring 22.

It will be appreciated that three conditions are required to be satisfied in order that the input shaft shall re-engage after a fail-safe operation. These are:

Firstly, the motor must start rotating in a direction that causes the elongated pinion 5 to wind downwards as illustrated. After a fail-safe operation, the spindle 4 will be in a position at its "safe" end of travel stop and limit switch circuit logic normally provided will ensure that the motor can only be started in a direction such that the spindle 4 is extending. For the example, as illustrated, this requires a clockwise rotation on shaft 2 with a corresponding right-handed helix on pinion 5.

Secondly, the helical gear wheel 6 provides the reacting force necessary to cause the elongated pinion 5 to descend and clutch into the pinion 7. This reacting force on the helical gear mesh is generated by (a) the normal friction of the spindle 4 as it starts to move in its bearings and seals; (b) the significant inertia of the spindle assembly together with the external equipment to which it is coupled provides a substantial reactory force at the gear mesh as the spindle angular velocity builds up. This force is directly proportional to the angular acceleration of the spindle.

Thirdly, the helix lead angle on the elongated pinion 5 must be sufficiently large to overcome the friction angle generated at the gear mesh so that the resultant force triangle will produce a thrust in the downward direction on the elongated pinion 5.

The actuator can then be operated normally in either direction by the motor 3—the holding magnet 39 being left continuously in its engaged state. From this "engaged drive" state, the "fail-safe" condition can be regained by removing power from both the holding magnet and the motor. It should be noted that, in the event of a motor failure by seizure of the motor shaft, the actuator will still be able to be brought into its fail-safe state by removing power from the holding magnet only.

It will be appreciated that, in the case of an actuator supplied with fluid power driving means in place of the electric motor 3, the electromagnet 39 with its pole piece 38 can be replaced by a fluid operated piston and cylinder assembly or flexible diaphragm assembly without departing from the scope of this invention.

In this context, the expression "fluid operated" refers to the use of either compressible gases or non-compressible liquids as the energy transfer medium.

For certain fail-safe applications where the actuator is required to be operated under water and, in particular, in association with valves and other equipment installed at or near the sea bed, it is possible to replace the force produced by the spring 22 by a force derived from the hydrostatic pressure of the surrounding water. A modification to the lower end of the actuator, to cover this alternative design is shown in FIG. 3.

Figure 3:
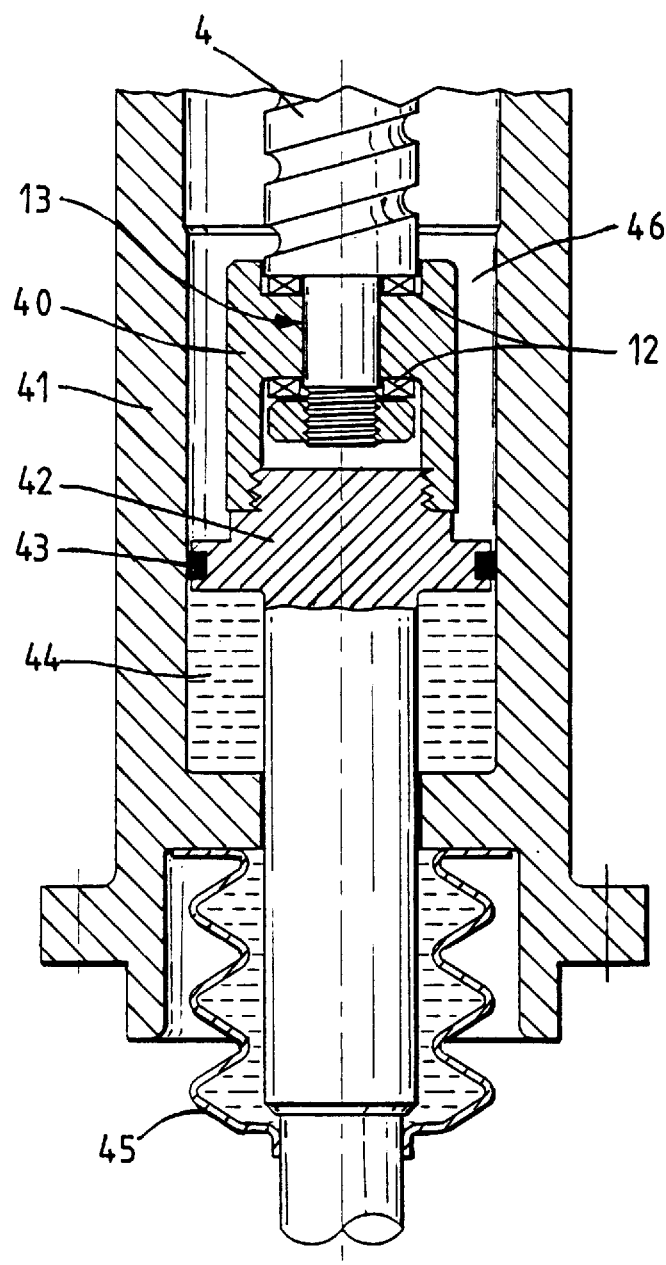
FIG. 3 is a part-section showing another modification of the first embodiment adapted for use in undersea actuator installations.

Referring to FIG. 3, the rotating end of the spindle 4 is provided with a bearing block 40, incorporating a spindle end journal bearing 13 and bi-directional thrust bearing set 12. The spindle end assembly is the same, or similar, to that shown in FIG. 1, but is adapted to operate within an extension 41 of the actuator housing. A piston and shaft extension assembly 42 with sealing member 43 is screwed, or otherwise fixed into the bearing block 40. The piston operates in a cylinder formed in the actuator extension 41.

The lower side, as illustrated, of the piston and shaft extension 42 is in contact with the hydrostatic pressure of water surrounding the actuator. The water may be directly in contact with the piston, but preferably a hydraulic oil medium 44 and flexible bellows 45, as shown, are provided in order to isolate the water from the internal working parts of the actuator.

The internal air space 46 of the actuator will be filled with air or other gas at a pressure at or near sea level atmospheric pressure so that the resulting pressure difference across the piston assembly 42, when the actuator is submerged below the water surface, will provide an upward, as drawn, force on the spindle 4 equivalent to the force provided by the spring 22 illustrated in FIG. 1.

Figure 2:
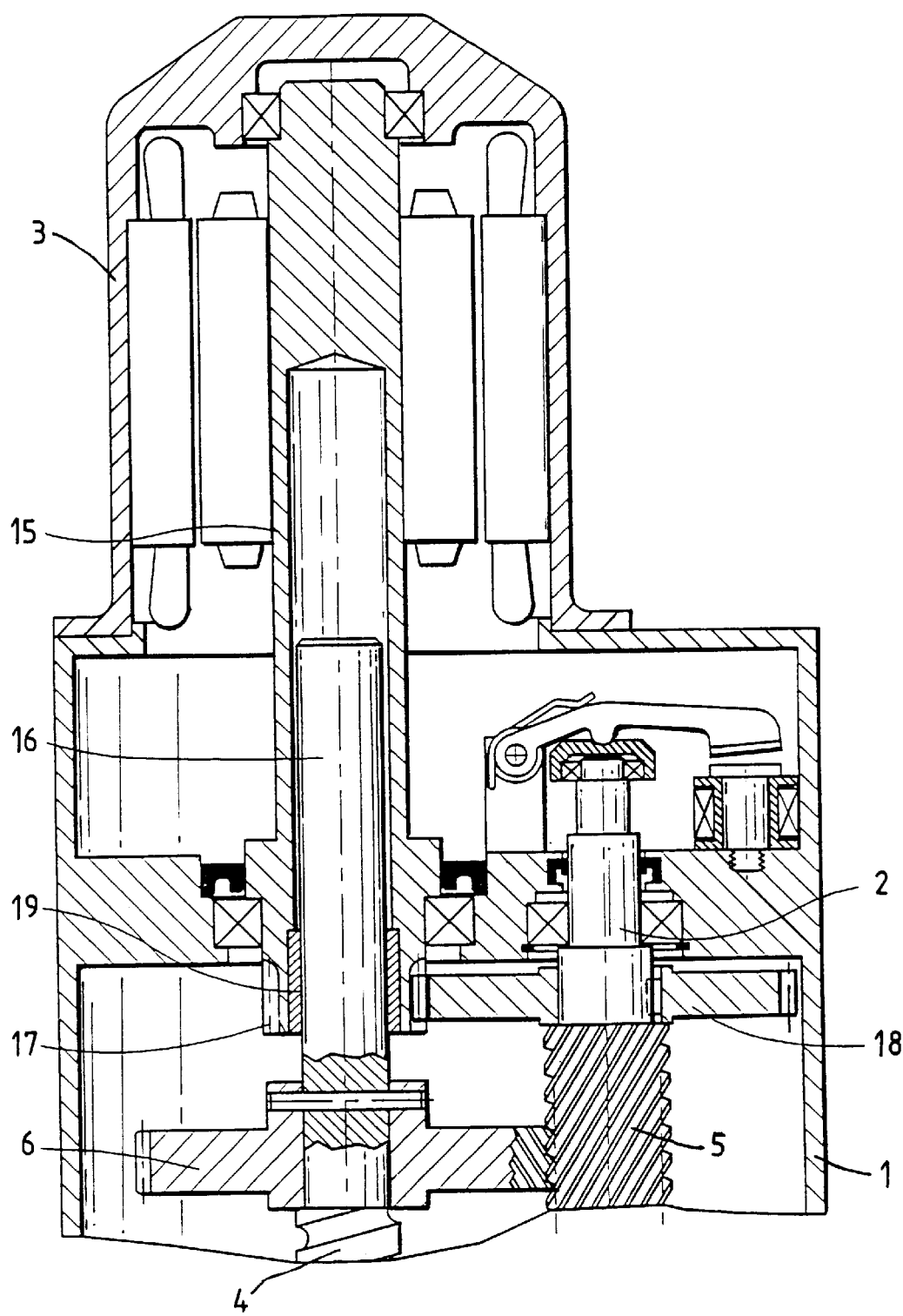
FIG. 2 is a part-section showing one modification of the first embodiment.
Figure 4:
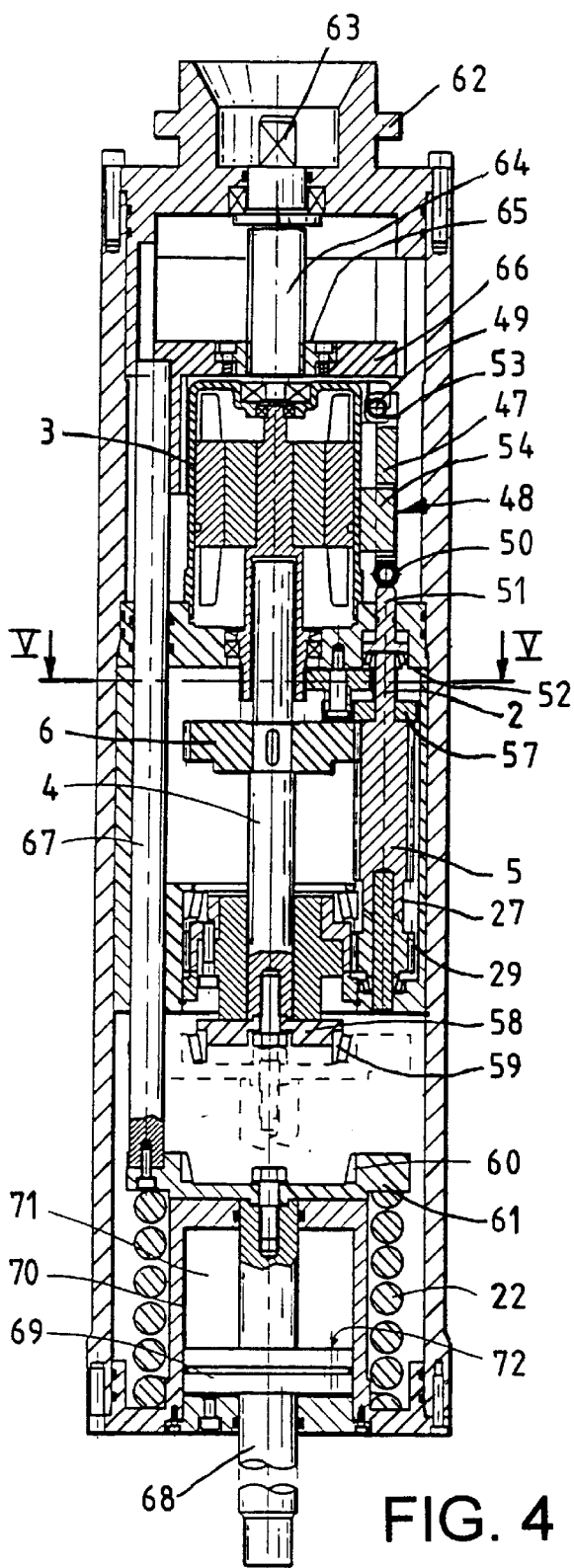
FIG. 4 is a longitudinal section through the second embodiment, which is designed particularly for a down hole, or undersea valve actuator.
Figure 5:
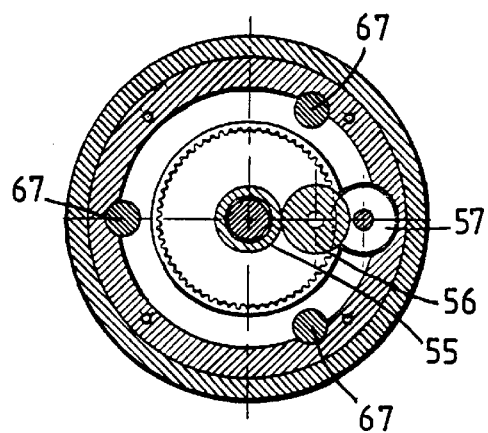
FIG. 5 is a cross-sectional view of the second embodiment taken on the plane V—V of FIG. 5.

Referring to FIGS. 4 and 5, it should be mentioned that for down-hole and undersea applications it is important to keep the overall cross-sectional dimension of the valve actuator as small as possible, which can be achieved with the modification described hereinbefore with reference to FIG. 2. Furthermore, in undersea applications, particularly in deep-sea conditions, it is important to be able to operate the valve actuator in the event of a mechanical or electrical failure by the use of a "remote operating vehicle" (R.O.V.). For this the valve actuator is normally provided with a standard attachment flange and shaft coupling of such a design that the R.O.V. can be manoeuvred, by remote control means, and attached to the actuator flange and coupling. The power source in the R.O.V. can then be used to operate the actuator, over-riding the failed mechanical or electrical mechanism in the normal actuator drive system.

In the second embodiment, the arrangement of the actuator drive and the manner in which it operates is similar to that described in FIGS. 1 to 3 except that the clutch holding magnet and associated items 32 to 39 in FIG. 1 have been re-positioned to lie alongside the motor 3. The lever 47 which carries an armature 48 is attached to the motor housing by a pivot 49. The free end of the lever 47 is provided with a roller 50 which, in the normal operating position, holds the clutch halves 27, 29 into engagement, with the electromagnet energised, by locking a tappet 51 and a thrust bearing 52 in the downward position. A light clock spring 53 is provided round the pivot 49 and acts on the lever to urge the armature 48 towards the pole piece of an electromagnet 54. In the fail-safe mode when the shaft 2 is being urged in an upward direction by the spring 22 acting on the gear 6 and hence on the helical mesh between gear 6 and pinion 5, the off-set of the pivot 49 from the thrust axis of the shaft 2 and roller 50 is sufficient to release the lever 47 and hence, the clutch, as soon as the electromagnet is de-energised.

The drive from the motor 3 to the shaft 2, shown in FIG. 5, is achieved by the use of a two-mesh gear train comprising a motor pinion 55, an idler gear cluster 56 and a driven gear 57 which is attached to the shaft 2. The use of the additional idler gear cluster 56 is to avoid the need to provide a large driven gear on shaft 2 (see FIG. 2 gear 18) which would increase the overall diameter of the actuator housing. The operation of the normal drive and the resulting axial movement of the spindle 4 is now as previously described with reference to FIG. 1.

In order to achieve an over-ride facility, using a R.O.V. and drive attachment, the actuator spindle 4 terminates in an upper thrust plate 58 carrying a taper roller thrust bearing. The rollers, roller cage and an inner track ring 59 of this bearing are held in the upper thrust plate, whilst an outer track ring 60 is held in a recess in a lower thrust plate 61, which is connected to an auxiliary output shaft 68. In the normal operating condition (R.O.V. not present) the two halves of the thrust bearing 59, 60 are in engagement, being held together by the spring 22. In FIG. 4 the lower half of the thrust bearing assembly has been shown in chain dotted outline because, for clarity, FIG. 4 illustrates the position of the mechanism after a R.O.V. operation.

The over-ride action of the R.O.V. is as follows:

The R.O.V. is attached to an upper flange 62 of the actuator with the R.O.V. output shaft being coupled to the upper end of an auxiliary drive shaft 63. This shaft carries a screw thread 64 and a drive nut 65 attached to an auxiliary thrust plate 66. Rotation of the auxiliary drive shaft 63 with the screw thread 64 causes the auxiliary thrust plate 66 with the nut 65 to descend (as illustrated in FIG. 4). This, in turn, drives the lower thrust plate 61 downwards by transferring the motion via three thrust rods 67. The two halves of the spindle thrust bearing 58, 61 are therefore separated, the spring 22 being compressed against its bias and the auxiliary output shaft 68 moving downwards independently of the position of the spindle 4.

To return to normal operating mode, the R.O.V. rotation is reversed allowing the auxiliary thrust plate 66 to return to its upper parked position. The spring 22 will then provide a force to withdraw the auxiliary output shaft 68 and re-engage the two halves of the thrust bearing 59, 60. The upper ends of the thrust rods 67 are not attached to the auxiliary thrust plate 66 so are free to move axially, in normal drive mode, whilst this plate is left in its upper parked position.

In order to prevent a too rapid failsafe operation which may cause damage to the actuator or valve, a fluid damper is provided in the space at the centre of the spring 22. The damper consists of a piston and piston seal assembly 69 which is fixed, or integral with the auxiliary output shaft 68 and which operates within a closed cylinder 70. The space 71 within the cylinder may be filled with air or any other gas or with a liquid—typically hydraulic oil. The damping action is provided by the small orifice 72 which allows fluid to pass from one side of the piston 69 to the other side.

The presence of the damper assembly allows the fail-safe operation to be achieved in a controlled manner the speed being determined by the size of the orifice 72. It is possible, therefore, to use the fail-safe operation as the normal closing operation for the valve operated by the actuator. Under this mode of operation it is only necessary to run the motor 3 in one direction, thus saving the cost and complexity of having to provide a reversing contactor set in the motor control circuit.

It will be appreciated that this second embodiment of actuator can be modified for use on land or at the sea surface by providing a handwheel to be fitted to the auxiliary drive shaft 63, either directly coupled, or operating the shaft via a worm drive gear box.

We claim:

1. A linear actuator comprising an output shaft having a pair of driven wheels mounted thereon, one of said pair of driven wheels being rotatably mounted in a fixed plane and having a drive nut for an associated thread on said output shaft, the other of said pair of driven wheels being rotatably fixed to said output shaft, and an input shaft in side-by-side relationship with said output shaft, said input shaft being adapted to be rotated by a suitable power source, said input shaft providing a drive wheel for each of said driven wheels, the ratio between each drive and driven wheel set being chosen to rotate the driven wheels at different speeds in the same rotational direction to produce a controlled axial movement of said output shaft in a direction depending upon the relative rotation of said driven wheels, wherein said other driven wheel and the drive wheel of its set are in the form of meshing helical gear wheels, and wherein a fail-safe arrangement is provided comprising a clutch between the drive wheels of the input shaft, a back-drive for said output shaft, and biasing means for effecting a back-drive, the arrangement being such that the meshing helical gears impart an axial force to engage the clutch only while power is supplied and the biasing means are operative to back-drive the output shaft to a fail-safe position when the power is terminated.

2. An actuator according to claim 1, wherein an electromagnet or other suitable force applying means is provided and adapted to maintain the clutch in engagement when power is terminated.

3. An actuator according to claim 1, wherein said other driven wheel is axially fixed on said output shaft, whereby the speed difference between the driven wheels will cause this wheel and hence the output shaft to move axially towards or away from said one driven wheel depending upon the relative rotation of said driven wheels.

4. An actuator according to claim 1, wherein said other driven wheel is also in a fixed plane, and wherein said output shaft is axially movable relative to this driven wheel via an axially extending key/keyway arrangement, whereby the speed difference between the driven wheels will cause movement of the output shaft in an axial direction depending upon the relative rotation of the two driven wheels.

5. An actuator according to claim 1, wherein the input and output shafts are parallel and the speed difference is achieved by using different tooth sizes/numbers for each drive/driven wheel set.

6. An actuator according to claim 1, wherein the back drive comprises a recirculating ball nut, or other low friction contact device, between the drive nut and associate thread to facilitate the action of the biasing means.

7. An actuator according to claim 1, for use in deep underwater applications, wherein the biasing means comprise a piston/cylinder arrangement in which the cylinder is maintained at a controlled pressure substantially lower than the surrounding water pressure to produce a continuous biasing force.

8. An actuator according to claim 1, wherein said power source comprises a motor with a hollow drive spindle in axial alignment with the output shaft for accommodating axial movement of said output shaft.

9. An actuator according to claim 1, for undersea application where a remote operating vehicle (R.O.V.) is provided in case of breakdown, wherein an auxiliary drive shaft is provided which is connected at one end to the drive end of the actuator output shaft, the other end being adapted to be coupled to the drive of the R.O.V., an auxiliary output shaft is provided at the output end of said actuator output shaft, and a thrust bearing is provided which in normal operation is arranged to maintain the actuator output shaft and the auxiliary drive shaft in the event of a breakdown providing a force which overcomes the biasing means to disengage the thrust bearing and permit independent R.O.V. operation of said auxiliary output shaft.

10. An actuator according to claim 9, wherein said thrust bearing is positioned between the output end of said actuator output shaft and said auxiliary output shaft, and the thrust bearing is in separable halves which are normally held in driving engagement by said biasing means, and the force provided by connection of said R.O.V. causing said halves to separate.

* * * * *